United States Patent
Govari et al.

(10) Patent No.: US 8,986,300 B2
(45) Date of Patent: Mar. 24, 2015

(54) IRRIGATED ELECTRODES WITH ENHANCED HEAT CONDUCTION

(75) Inventors: Assaf Govari, Haifa (IL); Christopher Thomas Beeckler, Brea, CA (US); Athanassios Papaioannou, Los Angeles, CA (US); Ariel Garcia, Glendora, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 346 days.

(21) Appl. No.: 13/531,861

(22) Filed: Jun. 25, 2012

(65) Prior Publication Data

US 2013/0345698 A1 Dec. 26, 2013

(51) Int. Cl.
*A61B 18/18* (2006.01)
*A61B 18/14* (2006.01)
*A61B 17/00* (2006.01)
*A61B 18/00* (2006.01)
*A61B 19/00* (2006.01)

(52) U.S. Cl.
CPC .... *A61B 18/1492* (2013.01); *A61B 2017/00318* (2013.01); *A61B 2018/00029* (2013.01); *A61B 2018/00357* (2013.01); *A61B 2018/00577* (2013.01); *A61B 2018/00815* (2013.01); *A61B 2018/00821* (2013.01); *A61B 2018/00839* (2013.01); *A61B 2019/5259* (2013.01); *A61B 2218/002* (2013.01)
USPC ........................................... 606/41; 607/116

(58) Field of Classification Search
None
See application file for complete search history.

(56) References Cited

U.S. PATENT DOCUMENTS

| | | |
|---|---|---|
| 5,730,127 A | 3/1998 | Avitall |
| 5,807,395 A | 9/1998 | Mulier et al. |
| 6,030,379 A | 2/2000 | Panescu et al. |
| 6,226,542 B1 | 5/2001 | Reisfeld |
| 6,301,496 B1 | 10/2001 | Reisfeld |
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,756,576 B2 | 7/2010 | Levin |
| 8,475,450 B2 | 7/2013 | Govari et al. |
| 2009/0093811 A1 | 4/2009 | Koblish et al. |
| 2009/0149848 A1 | 6/2009 | Werneth et al. |
| 2010/0016848 A1 | 1/2010 | Desai |
| 2010/0030209 A1 | 2/2010 | Govari et al. |
| 2010/0168548 A1 | 7/2010 | Govari et al. |
| 2013/0339782 A1 | 12/2013 | Beverly |

OTHER PUBLICATIONS

European Search Report, Application No. 13173406.3-1659, 9 pages, dated Oct. 23, 2013.

*Primary Examiner* — Brian T Gedeon
(74) *Attorney, Agent, or Firm* — Wayne C. Jaeschke, Jr.

(57) ABSTRACT

A catheter adapted for insertion into a body of a subject has at least one electrode disposed on its distal section. The electrode is coupled to an energy source to ablate tissue that is placed in contact with the electrode. The electrode has a wall with a plurality of perforations formed therethrough, and has edges defining a peripheral section that is adjacent the edges and a central section remote from the edges, wherein the wall of the peripheral section is thicker than the wall of the central section. A lumen passing through the insertion tube is coupled to deliver a fluid to the tissue via the perforations. In operation, the electrode functions as an effective heat sink.

26 Claims, 5 Drawing Sheets

IRRIGATED ELECTRODES WITH ENHANCED HEAT CONDUCTION

BACKGROUND OF THE INVENTION

1. Field of the Invention

This invention relates to medical devices. More particularly, this invention relates to cooling of tissue contacted by an invasive probe within the body.

2. Description of the Related Art

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region along the pulmonary veins of the left atrium and in myocardial tissue associated with cardiac ganglionic plexi. In this condition, after unwanted signals are generated in the pulmonary veins or conducted through the pulmonary veins from other sources, they are conducted into the left atrium where they can initiate or continue arrhythmia.

Procedures for treating arrhythmia include disrupting the areas causing the arrhythmia by ablation, as well as disrupting the conducting pathway for such signals. Ablation of body tissue using electrical energy is known in the art. The ablation is typically performed by applying alternating currents, for example radiofrequency energy, to the electrodes, at a sufficient power to destroy target tissue. Typically, the electrodes are mounted on the distal tip or portion of an invasive probe or catheter, which is inserted into a subject. The distal tip may be tracked in a number of different ways known in the art, for example by measuring magnetic fields generated at the distal tip by coils external to the subject.

A known difficulty in the use of radiofrequency energy for cardiac tissue ablation is controlling local heating of tissue. There are tradeoffs between the desire to create a sufficiently large lesion to effectively ablate an abnormal tissue focus, or block an aberrant conduction pattern, and the undesirable effects of excessive local heating. If the radiofrequency device creates too small a lesion, then the medical procedure could be less effective, or could require too much time. On the other hand, if tissues are heated excessively then there could be local charring effects due to overheating. Such overheated areas can develop high impedance, and may form a functional barrier to the passage of heat. The use of slower heating provides better control of the ablation, but unduly prolongs the procedure.

Previous approaches to controlling local heating include the inclusion of thermocouples within the electrode and feedback control, signal modulation, local cooling of the catheter tip, and fluid-assisted techniques, for example irrigation of the target tissue during the energy application, using chilled fluids. Typical of the last approach is Mulier, et al. U.S. Pat. No. 5,807,395.

Commonly assigned U.S. Pat. No. 6,997,924, which is herein incorporated by reference, describes a technique of limiting heat generated during ablation by determining a measured temperature of the tissue and a measured power level of the transmitted energy, and controlling the power output level responsively to a function of the measured temperature and the measured power level.

More recently, commonly assigned U.S. Patent Application Publication No. 2010/0030209 by Govari et al., which is herein incorporated by reference, describes an insertion tube, having an outer surface with a plurality of perforations through the outer surface, which are typically about 100 μm in diameter, and are distributed circumferentially and longitudinally over the distal tip. A lumen passes through the insertion tube and is coupled to deliver a fluid to the tissue via the perforations.

Commonly assigned U.S. Patent Application Publication No. 2010/0168548 by Govari et al., describes a catheter having perforated electrodes that bulge above the outer surface of the catheter to permit an outflow of irrigating fluid.

SUMMARY OF THE INVENTION

The walls of currently used irrigating electrodes have a constant thickness along their entire length. During ablation, the two edges or peripheral regions of the electrodes may heat up excessively. This may result from poor irrigation, as the edges tend to be spaced apart from the irrigation holes and a higher density of the electric field lines at the peripheral zones, which form sharp conductive edges of the electrode, known as an "edge effect".

In the embodiments presented herein, the wall thickness of the electrodes is increased at the edges, providing a relatively greater thermal mass and providing increased heat absorption capacity compared to the central portion of the electrode. Consequently, during ablation there is a decreased rise in temperature at the ablation site, thereby minimizing the probability for blood coagulation, tissue scorching, and damage to the adjacent catheter structure.

There is provided according to embodiments of the invention an insertion tube or catheter, adapted for insertion into a body of a subject. The tube has at least one electrode disposed on its distal section, which is coupled to an energy source to apply energy to tissue that is placed in contact with the electrode. The electrode has a wall with a plurality of perforations formed therethrough, and has edges defining a peripheral section that is adjacent the edges and a central section remote from the edges, wherein the wall of the peripheral section is thicker than the wall of the central section. A lumen passing through the insertion tube is coupled to deliver a fluid to the tissue via the perforations.

According to one aspect of the device, the wall continually and gradually thickens from a point on the central section toward the peripheral section.

According to aspect of the device, the wall thickens in discrete stages from the central section toward the peripheral section.

According to still another aspect of the device, the wall of the central section has a uniform thickness.

According to an additional aspect of the device, the perforations of the electrode have diameters between 0.05 mm and 2.5 mm. According to still another aspect of the device, the diameters are between 0.5 and 2.5 mm. According to a further aspect of the device, there are up to sixty perforations.

According to yet another aspect of the device, the electrode is round in contour, and the wall thickens from the central section toward the peripheral section in all outward directions.

According to one aspect of the device, the electrode is elliptical in contour, and the wall thickens from the central section toward the peripheral section in all outward directions.

According to a further aspect of the device, a mass of the peripheral section is between three and five times a mass of the central section.

According to another aspect of the method, a mass of the peripheral section exceeds a mass of the central section and is up to twice the mass of the central section.

According to yet another aspect of the device, the electrode includes a plurality of ring electrodes linearly arranged on the distal section of the insertion tube.

According to an additional aspect of the device, the electrode bulges between 0.05 mm and 1.0 mm above the outer surface of the insertion tube.

Other embodiments of the invention provide methods that are carried out by the above-described device.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

EMBODIMENT 1

Figure 1:
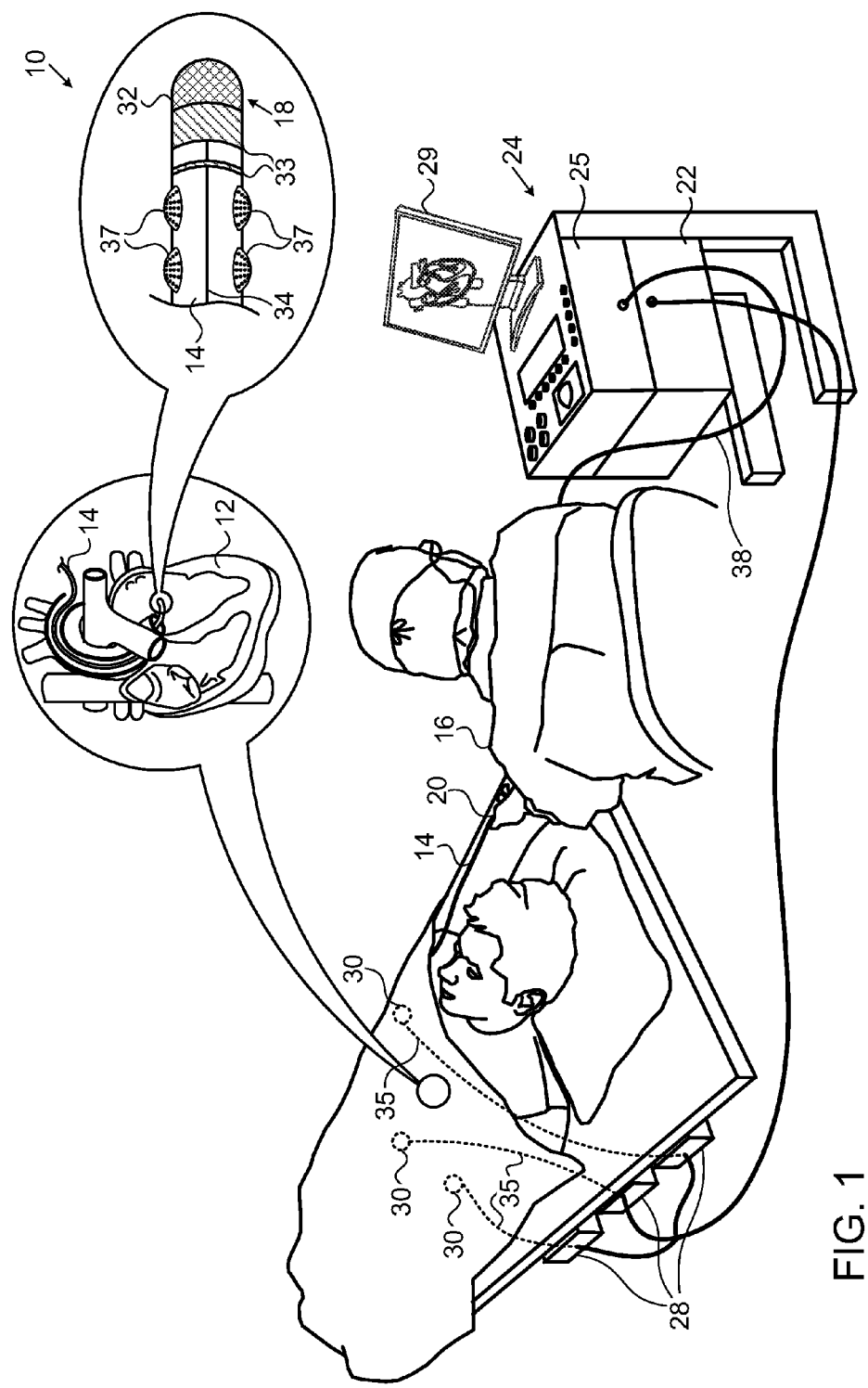
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with an embodiment of the invention. The system comprises a catheter 14, which is percutaneously inserted by an operator 16 through the patient's vascular system into a chamber or vascular structure of the heart 12. The operator 16, who is typically a physician, brings the catheter's distal portion or tip 18 into contact with the heart wall at an ablation target site. Optionally, electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathways causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24.

Ablation energy and electrical signals can be conveyed to and from the heart 12 through an ablation electrode 32 located at the distal tip 18 via cable 34 to the console 24. While a single ablation electrode 32 is shown, more than one can be present. Pacing signals and other control signals may be conveyed from the console 24 through the cable 34 and the ablation electrode 32 to the heart 12. Sensing electrodes 33, also connected to the console 24 are typically disposed near the ablation electrode 32 and have connections to the cable 34.

Wire connections 35 link the console 24 with body surface electrodes 30 and other components of a positioning subsystem. A temperature sensor (not shown), typically a thermocouple or thermistor, may be mounted on or near the ablation electrode 32 and to electrodes 37.

One or more electrodes 37 are distributed about the shaft of the catheter 14, generally along the distal segment. The electrodes 37 are adapted for enhanced heat conductance, which is useful when they are employed for ablation. However the electrodes 37 may be used as sensing electrodes or for pacing. The electrodes 37 typically bulge above the surface of the catheter, but may be flush with the surface of the catheter, so long as the wall thickness varies as described in the various embodiments hereinbelow. While a generally curved profile is shown in the example of FIG. 1, in some embodiments the electrodes may appear as a flat plateau above the surface of the catheter shaft when viewed in profile.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem of the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume its vicinity and sensing these fields at the catheter using field generating coils 28 and may include impedance measurement, as taught, for example in commonly assigned U.S. Pat. No. 7,756,576, which is herein incorporated by reference.

As noted above, the catheter 14 is coupled to the console 24, which enables the operator 16 to observe and regulate the functions of the catheter 14. Console 24 includes a processor, preferably a computer provided with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning subsystem to compute the position and orientation of the catheter 14 and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally placed catheter, which is inserted into the heart 12 and maintained in a fixed position relative to the heart 12. Conventional pumps and lines for circulating liquids through the catheter 14 for cooling the ablation site are provided.

Figure 2:
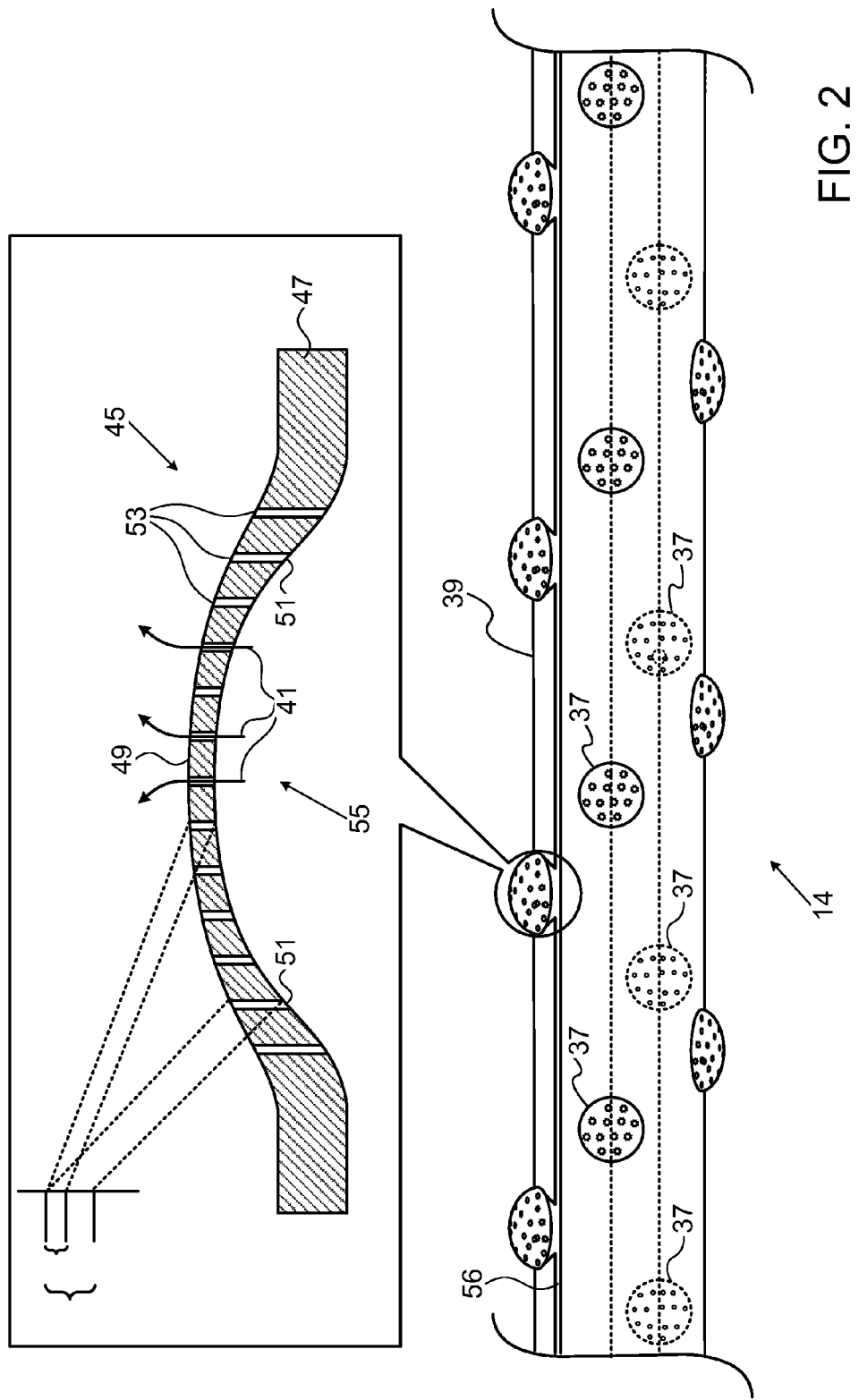
FIG. 2 is a detailed view of the distal portion of the catheter shown in FIG. 1, showing multiple electrodes distributed in linear arrays, in accordance with an embodiment of the invention.

Reference is now made to FIG. 2, which is a detailed view of the distal portion of the catheter 14, showing multiple electrodes 37 distributed in linear arrays about its shaft 39. The electrodes 37 may bulge between about 0.05-0.5 mm above the outer surface of the shaft 39 and have a generally rounded profile, forming a cap on the surface of the shaft. In some embodiments the electrodes 37 may have a larger bulge, up to 1 mm above the surface. The electrodes 37 may extend over 25-70 per cent of the circumference of the surface 41, as contrasted with a conventional ring electrode, which covers 100% of the circumference. The electrodes 37 may have a circular border contour. Alternatively, they may be elliptical in contour, as further described in commonly assigned application Ser. No. 12/345720, entitled "Dual-Purpose Lasso Catheter with Irrigation", which is herein incorporated by reference. The electrodes 37 may be 2-5 mm in dimension. These configurations provide substantial contact between the electrodes 37 and the cardiac tissue, lowering electrical resistance as compared with conventional electrodes. When the electrodes 37 are used for ablation, the reduced electrical resistance is particularly advantageous. In one embodiment, two of the electrodes 37 are selected for performing bi-polar ablation, e.g., radiofrequency ablation in which case a cable 43 may include wires individually leading to the electrodes 37.

As shown in a representative view, cross-section 45 has a generally curved contour, forming a bulge on the shaft 39. The bulge of the electrode increases the surface area that is in contact with the target tissue, and reduces electrical resistance when the electrodes are used for ablation. Wall 47 of the electrodes 37 has a non-uniform thickness. It is relatively thin at a central point 49, and thickens in all directions toward peripheral regions 51 adjacent the edges.

The wall 47 may thicken in a continual, gradual manner toward the edges of the electrodes 37. Alternatively, the wall 47 may thicken in discrete stages from the center toward the edges. In any case, the non-uniform thickness of the wall 47 provides enhanced heat conductance at the edges of the electrodes, which act as a heat sink. The heat sink helps to prevent thermal damage to the electrodes and to the surrounding areas on the shaft 39, and reduces the likelihood of undesired blood coagulation at or near the site of ablation. The shaft 39 is typically formed of plastic, and is susceptible to overheating.

The wall 47 is fenestrated by multiple small perforations 53 formed therethrough. Typically there are between 1 and 60 perforations having diameters of 0.5-2.5 mm. Alternatively, much smaller diameters of between 0.05-0.4 mm may be used in order to generate turbulent flow, as described in commonly assigned, co-pending application Ser. No. 13/339,782, entitled "Electrode Irrigation Using Micro-Jets", which is herein incorporated by reference. The perforations 53 are in fluid communication with an irrigating chamber 55, formed beneath the wall 47. The chamber 55 in turn is in fluid communication with an irrigation lumen 56 within the shaft 39, so that the fluid flows outward, through the perforations 53, as indicated by arrows 41. There may be a plurality of irrigation lumens in order to more conveniently supply the electrodes 37 when they are distributed about the circumference of the shaft 39.

EMBODIMENT 2

Figure 3:
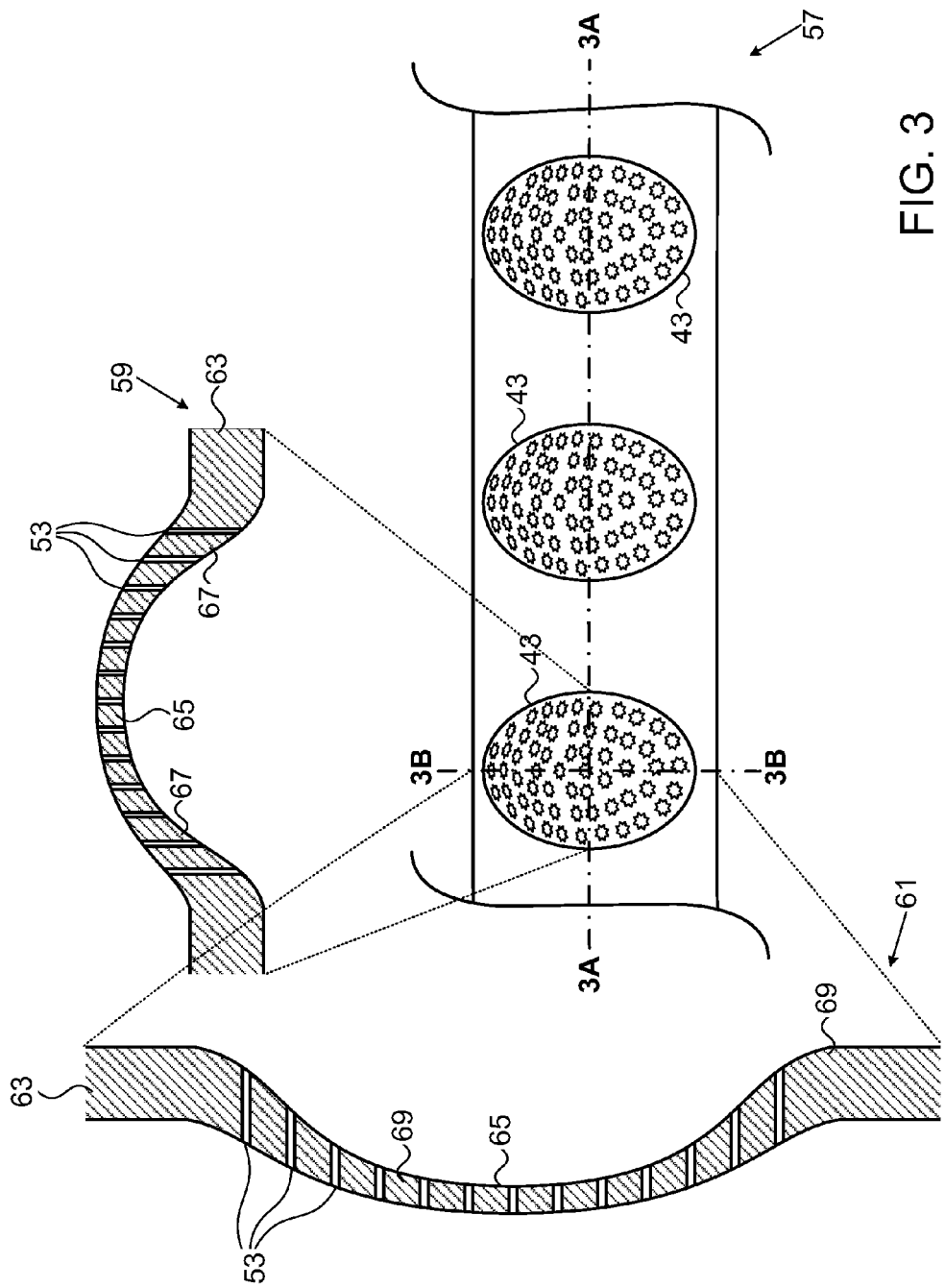
FIG. 3 is a composite view of the distal portion of a catheter, which is constructed in accordance with an alternate embodiment of the invention.

Reference is now made to FIG. 3, which is a composite view of the distal portion of a catheter 57, which is constructed in accordance with an alternate embodiment of the invention. The catheter 57 is similar to the catheter 14 (FIG. 1), except that raised, perforated electrodes 43 are elliptical rather than circular. In FIG. 3 the orientation of the ellipses is such that their major axes are perpendicular to the long axis of the catheter, shown as line 3A-3A. However, the electrodes 43 may be oriented such that their major axes are aligned with or parallel to line 3A-3A.

FIG. 3 shows sectional views 59, 61 of one of the electrodes 43 along lines 3A-3A and 3B-3B, respectively. In both cases, wall 63 is relatively thin at central point 65 and relatively thick in regions 67, 69 near the edges of the electrodes 43.

EMBODIMENT 3

Figure 4:
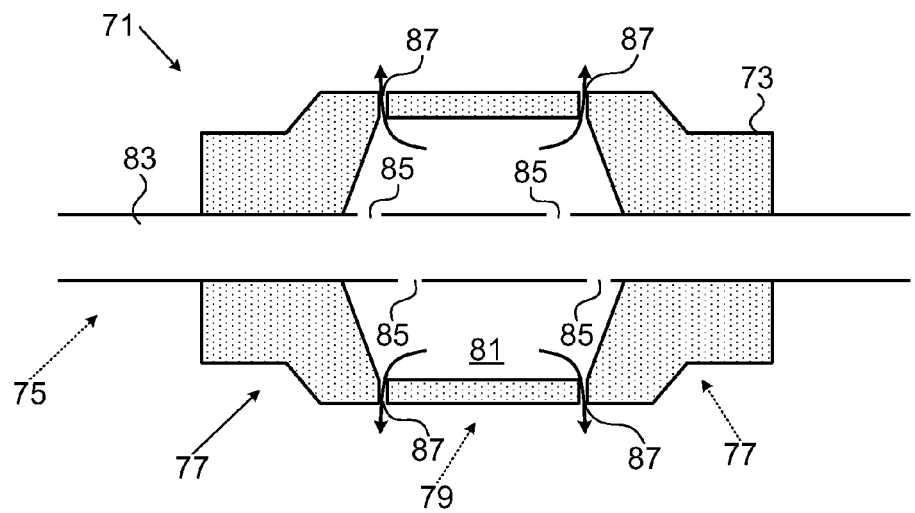
FIG. 4 is a sectional view of a segment of the distal portion of a catheter, which is constructed in accordance with an alternate embodiment of the invention.

Reference is now made to FIG. 4, which is a sectional view of a segment of the distal portion of a catheter 71, which is constructed in accordance with an alternate embodiment of the invention.

A perforated electrode 73 bulges above the catheter's outer surface 75 and may form a ring about the catheter shaft. The electrode 73 comprises relatively thick peripheral sections 77, a relatively thin central section 79 and an interior chamber 81. The wall thickness may vary as in the electrodes of the previous embodiments, i.e., gradually from center to edge, or in stepwise increments from center to edge. The chamber 81 is in fluid communication with a lumen 83, through which irrigating fluid is supplied to the chamber 81 via channels 85. The irrigating fluid escapes from the chamber 81 through orifices 87 where it cools the ablation site and in particular the central section 79. The peripheral sections 77 act as an excess heat sink, preventing overheating of the ablation site and the catheter structure itself during ablation.

The peripheral sections 77 have a greater thermal mass than the central section 79. The ratio can be 2:1, but preferably is at least 3:1, and may be as high as 5:1. A current embodiment has a ratio of approximately 3.5:1, in order that the peripheral sections 77 function effectively as improved heat sinks in comparison to electrodes having uniform wall thickness. The electrode 73 and the electrodes shown in other embodiments herein may be made from an electrically conductive biocompatible material. For example, it could be made out of platinum, gold, other noble metals, and alloys thereof in a variety of compositions.

Figure 5:
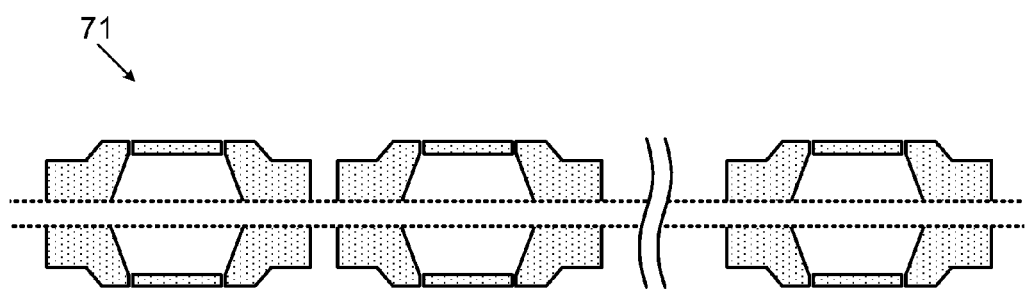
FIG. 5 shows a linear arrangement of multiple electrodes on the distal portion of a catheter, in accordance with an alternate embodiment of the invention.

Reference is now made to FIG. 5, which shows a linear arrangement of the multiple electrodes 73 on the distal portion of the catheter 71, in accordance with an embodiment of the invention.

EMBODIMENT 4

Figure 6:
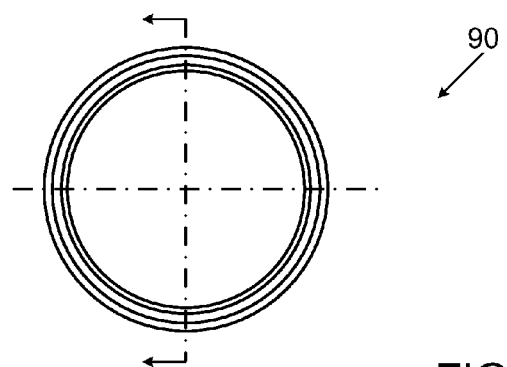
FIG. 6 is a cross-sectional view through an irrigation ring of a catheter in accordance with the embodiments shown in FIG. 4 and FIG. 5.
Figure 7:
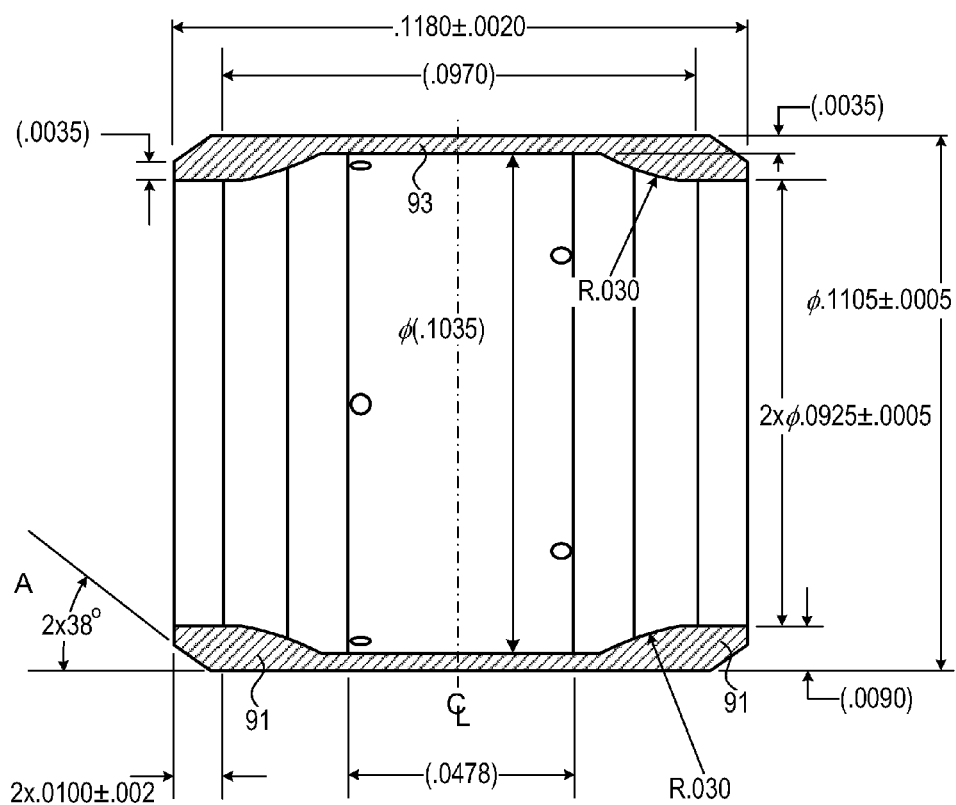
FIG. 7 is a detailed longitudinal sectional view through the irrigation ring shown in FIG. 6, indicating various typical dimensions.

Reference is now made to FIG. 6, which is a cross sectional view of an irrigation ring electrode 90 in accordance with an alternate embodiment of the invention. Reference is now made to FIG. 7, which is a detailed longitudinal sectional view of the irrigation ring electrode shown in FIG. 6. Peripheral sections 91 are beveled at an angle A (2×38°). The peripheral sections 91 are more than twice as thick as central section 93 (0.009" vs. 0.0035").

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A medical device, comprising:
an insertion tube, having a distal section for insertion into a body of a subject;
at least one electrode disposed on the distal section of the insertion tube and coupled to an energy source to apply energy to tissue inside the body, the electrode having an outer surface and a wall with a plurality of perforations formed therethrough, the electrode having edges defining a peripheral section that is adjacent the edges and a central section remote from the edges, wherein the wall of the peripheral section is thicker than the wall of the central section; and
a lumen passing through the insertion tube and coupled to deliver a fluid to the tissue via the perforations.

2. The device according to claim 1, wherein the wall continually and gradually thickens from a point on the central section toward the peripheral section.

3. The device according to claim 1, wherein the wall thickens in discrete stages from the central section toward the peripheral section.

4. The device according to claim 1, wherein the wall of the central section has a uniform thickness.

5. The device according to claim 1, wherein the perforations have diameters are between 0.05 mm and 2.5 mm.

6. The device according to claim 5, wherein the diameters are between 0.5 and 2.5 mm.

7. The device according to claim 1, wherein the plurality of perforations comprises up to sixty perforations.

8. The device according to claim 1, wherein the electrode is round in contour, and wherein the wall thickens from the central section toward the peripheral section in all outward directions.

9. The device according to claim 1, wherein the electrode is elliptical in contour, and wherein the wall thickens from the central section toward the peripheral section in all outward directions.

10. The device according to claim 1, wherein a mass of the peripheral section is between three and five times a mass of the central section.

11. The method according to claim 1, wherein a mass of the peripheral section exceeds a mass of the central section and is up to twice the mass of the central section.

12. The device according to claim 1, wherein the electrode comprises a plurality of ring electrodes linearly arranged on the distal section of the insertion tube.

13. The device according to claim 1, wherein the electrode bulges between 0.05 mm and 1.0 mm above the outer surface of the insertion tube.

14. A method for cardiac ablation, comprising the steps of:
introducing an insertion tube, having a distal section into a heart of a subject, the insertion tube having at least one electrode disposed on the distal section of the insertion tube and coupled to an energy source, the electrode having an outer surface and a wall with a plurality of perforations formed therethrough, the electrode having edges defining a peripheral section that is adjacent the edges and a central section remote from the edges, wherein the wall of the peripheral section is thicker than the wall of the central section, and a lumen passing through the insertion tube and coupled to deliver a fluid via the perforations;
locating the distal section of the insertion tube in proximity to a target in the heart;
analyzing electrical signals received from the target via the insertion tube to make a determination that the electrical signals are indicative of abnormal electrical conduction within the heart; and
responsively to the determination conducting energy into the heart via the electrode to thereby affect the abnormal electrical conduction.

15. The method according to claim 14, wherein the wall continually and gradually thickens from a point on the central section toward the peripheral section.

16. The method according to claim 14, wherein the wall thickens in discrete stages from the central section toward the peripheral section.

17. The method according to claim 14, wherein the wall of the central section has a uniform thickness.

18. The method according to claim 14, wherein the perforations have diameters between 0.05 mm and 2.5 mm.

19. The method according to claim 18, wherein the diameters are between 0.5 and 2.5 mm.

20. The method according to claim 14, wherein the plurality of perforations comprises up to sixty perforations.

21. The method according to claim 14, wherein the electrode is round in contour, and wherein the wall thickens from the central section toward the peripheral section in all outward directions.

22. The method according to claim 14, wherein the electrode is elliptical in contour, and wherein the wall thickens from the central section toward the peripheral section in all outward directions.

23. The method according to claim 14, wherein a mass of the peripheral section exceeds a mass of the central section and is up to twice the mass of the central section.

24. The method according to claim 14, wherein a mass of the peripheral section is between three and five times a mass of the central section.

25. The method according to claim 14, wherein the electrode comprises a plurality of ring electrodes linearly arranged on the distal section of the insertion tube.

26. The method according to claim 14, wherein the electrode bulges between 0.05 mm and 1.0 mm above the outer surface of the insertion tube.

* * * * *